(12) United States Patent
Kamtekar

(10) Patent No.: US 12,256,638 B2
(45) Date of Patent: Mar. 18, 2025

(54) PHOTOACTIVE COMPOUND

(71) Applicant: Sumitomo Chemical Co., Ltd., Tokyo (JP)

(72) Inventor: Kiran Kamtekar, Godmanchester (GB)

(73) Assignee: Sumitomo Chemical Co., Ltd., Tokyo (JP)

( * ) Notice: Subject to any disclaimer, the term of this patent is extended or adjusted under 35 U.S.C. 154(b) by 882 days.

(21) Appl. No.: 17/297,997

(22) PCT Filed: Nov. 29, 2019

(86) PCT No.: PCT/GB2019/053390
§ 371 (c)(1),
(2) Date: May 27, 2021

(87) PCT Pub. No.: WO2020/109821
PCT Pub. Date: Jun. 4, 2020

(65) Prior Publication Data
US 2021/0399235 A1 Dec. 23, 2021

(30) Foreign Application Priority Data
Nov. 30, 2018 (GB) ..................... 1819623

(51) Int. Cl.
| | | |
|---|---|---|
| *H01L 51/00* | (2006.01) | |
| *C07D 495/04* | (2006.01) | |
| *G01N 21/64* | (2006.01) | |
| *H10K 85/60* | (2023.01) | |
| *H10K 30/30* | (2023.01) | |
| *H10K 71/15* | (2023.01) | |
| *H10K 71/40* | (2023.01) | |

(52) U.S. Cl.
CPC ....... *H10K 85/6576* (2023.02); *C07D 495/04* (2013.01); *G01N 21/645* (2013.01); *H10K 85/6572* (2023.02); *H10K 30/30* (2023.02); *H10K 71/15* (2023.02); *H10K 71/441* (2023.02)

(58) Field of Classification Search
CPC ............. H01L 51/0074; H01L 51/0072; H01L 51/4253; C07D 495/04; G01N 21/645
See application file for complete search history.

(56) References Cited

U.S. PATENT DOCUMENTS 5,112,759 A * 5/1992 Senoo ................. G03G 5/0668
430/72
2017/0358766 A1 12/2017 Hammond et al.
2019/0157581 A1 5/2019 Seifrid et al.
2019/0267545 A1 8/2019 Yamaguchi et al.

FOREIGN PATENT DOCUMENTS

JP    H03-12658 A    1/1991
JP    2018078242 A   5/2018

OTHER PUBLICATIONS

JP 2021-5301113, Jul. 5, 2023, Japanese Office Action.
International Search Report and Written Opinion mailed Feb. 20, 2020 in connection with International Application No. PCT/GB2019/053390.
Combined Search and Examination Report dated May 20, 2019 in connection with GB Application No. 1819623.8.
Japanese Office Action dated Jul. 5, 2023, in connection with Japanese Application No. 2021-530113.

* cited by examiner

*Primary Examiner* — Robert D Harlan
(74) *Attorney, Agent, or Firm* — Wolf, Greenfield & Sacks, P.C.

(57) ABSTRACT

A compound of formula (I): EAG-EDG-EAG (I) wherein EDG is an electron-donating group comprising a polycyclic heteroaromatic group and each EAG is an electron-accepting group of formula (II): (II) wherein $R^{10}$ in each occurrence is H or a substituent; --- is a bond to EDG; and each $X^1$-$X^4$ is independently $CR^{11}$ or N wherein $R^{11}$ in each occurrence is H or a substituent, with the proviso that at least one occurrence of at least one of $X^1$-$X^4$ is N. The compound may be used as an acceptor in a bulk heterojunction layer of an organic photodetector.

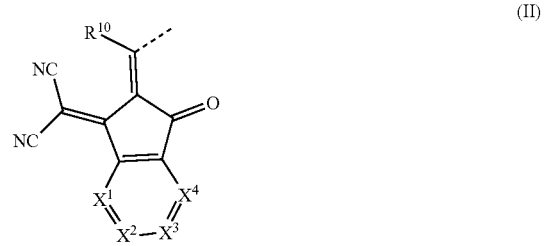

19 Claims, 2 Drawing Sheets

PHOTOACTIVE COMPOUND

RELATED APPLICATIONS

This Application is a national stage filing under 35 U.S.C. § 371 of international PCT application no. PCT/GB2019/053390, filed Nov. 29, 2019, which claims priority to United Kingdom patent application no. GB 1819623.8, filed Nov. 30, 2018, each of which is incorporated herein by reference in its entirety.

BACKGROUND

Embodiments of the present disclosure relate to photoactive compounds and their use in organic electronic devices, in particular organic photodetectors.

A range of organic electronic devices comprising organic semiconductor materials are known, including organic light-emitting devices, organic field effect transistors, organic photovoltaic devices and organic photodetectors (OPDs).

WO 2018/065352 discloses an OPD having a photoactive layer that contains a small molecule acceptor which does not contain a fullerene moiety and a conjugated copolymer electron donor having donor and acceptor units.

WO 2018/065356 discloses an OPD having a photoactive layer that contains a small molecule acceptor which does not contain a fullerene moiety and a conjugated copolymer electron donor having randomly distributed donor and acceptor units.

Yao et al, "Design, Synthesis, and Photovoltaic Characterization of a Small Molecular Acceptor with an Ultra-Narrow Band Gap", Angew Chem Int Ed Engl. 2017 Mar. 6; 56(11):3045-3049 discloses a non-fullerene acceptor with a band gap of 1.24 eV.

SUMMARY

A summary of aspects of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects and/or a combination of aspects that may not be set forth.

Embodiments of the present disclosure provide a compound of formula (I):

wherein EDG is an electron-donating group comprising a polycyclic heteroaromatic group and each EAG is an electron-accepting group of formula (II):

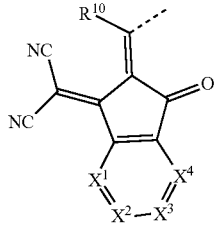

wherein $R^{10}$ in each occurrence is H or a substituent;
---- is a bond to EDG; and each $X^1$-$X^4$ is independently $CR^{11}$ or N wherein $R^{11}$ in each occurrence is H or a substituent, with the proviso that at least one occurrence of at least one of $X^1$-$X^4$ is N.

The present inventors have found that compounds of formula (I) may be capable of absorbing light at long wavelengths, e.g. greater than 750 nm, optionally greater than 900 nm, optionally up to about 1500 nm allowing for use of these compounds in organic photodetectors, particularly in a photosensor containing such an OPD and a near infra-red light source.

Accordingly, in some embodiments, there is provided a composition containing an electron-accepting (n-type) compound as described herein and an electron donor (p-type) compound.

In some embodiments there formulation comprising a composition as described herein dissolved or dispersed in one or more solvents.

In some embodiments there is provided an organic photodetector having: an anode; a cathode; and a photosensitive organic layer disposed between the anode and cathode wherein the photosensitive organic layer contains a donor compound and an acceptor compound of formula (I).

In some embodiments, there is provided a method of forming an organic photodetector as described herein comprising formation of the photosensitive organic layer over one of the anode and cathode and formation of the other of the anode and cathode over the photosensitive organic layer.

In some embodiments, there is provided a circuit comprising an organic photodetector as described herein, and at least one of a voltage source for applying a reverse bias to the organic photodetector and a device configured to measure photocurrent generated by the photodetector.

In some embodiments, there is provided a photosensor comprising a light source and an organic photodetector as described herein configured to detect light emitted from the light source.

In some embodiments, there is provided a method of determining the presence and/or concentration of a target material in a sample, the method comprising illuminating the sample and measuring a response of an organic photodetector as described herein which is configured to receive light emitted from the sample upon illumination.

DESCRIPTION OF DRAWINGS

The disclosed technology and accompanying figures describe some implementations of the disclosed technology.

Figure 1:
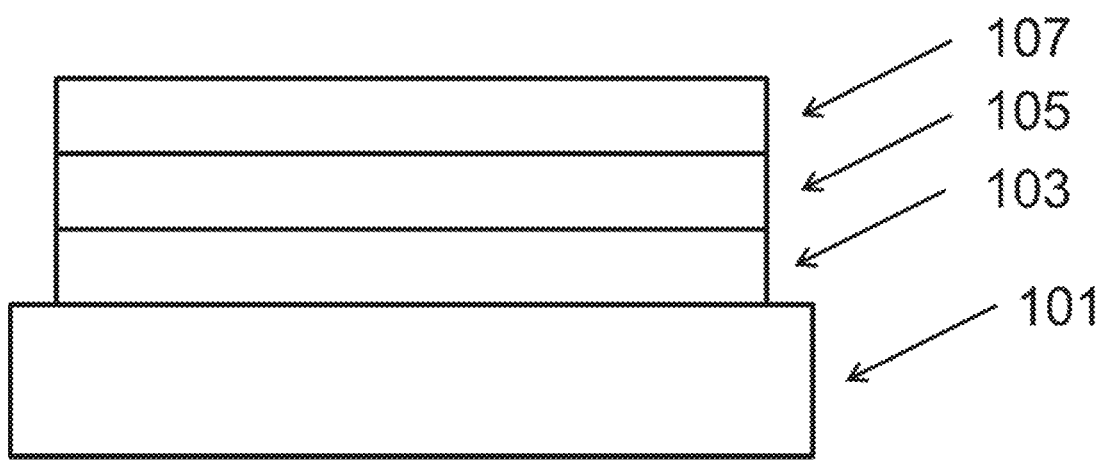
FIG. 1 illustrates an organic photodetector according to some embodiments.

The drawings are not drawn to scale and have various viewpoints and perspectives. The drawings are some implementations and examples. Additionally, some components and/or operations may be separated into different blocks or combined into a single block for the purposes of discussion of some of the embodiments of the disclosed technology.

Moreover, while the technology is amenable to various modifications and alternative forms, specific embodiments have been shown by way of example in the drawings and are described in detail below. The intention, however, is not to limit the technology to the particular implementations described. On the contrary, the technology is intended to cover all modifications, equivalents, and alternatives falling within the scope of the technology as defined by the appended claims.

DETAILED DESCRIPTION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, electromagnetic, or a combination thereof. Additionally, the words "herein," "above," "below," and words of similar import, when used in this application, refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

The teachings of the technology provided herein can be applied to other systems, not necessarily the system described below. The elements and acts of the various examples described below can be combined to provide further implementations of the technology. Some alternative implementations of the technology may include not only additional elements to those implementations noted below, but also may include fewer elements.

These and other changes can be made to the technology in light of the following detailed description. While the description describes certain examples of the technology, and describes the best mode contemplated, no matter how detailed the description appears, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while some aspect of the technology may be recited as a computer-readable medium claim, other aspects may likewise be embodied as a computer-readable medium claim, or in other forms, such as being embodied in a means-plus-function claim.

In the following description, for the purposes of explanation, numerous specific details are set forth in order to provide a thorough understanding of implementations of the disclosed technology. It will be apparent, however, to one skilled in the art that embodiments of the disclosed technology may be practiced without some of these specific details.

FIG. 1 illustrates an OPD according to some embodiments of the present disclosure. The OPD comprises a cathode 103, an anode 107 and a bulk heterojunction layer 105 disposed between the anode and the cathode. The OPD may be supported on a substrate 101, optionally a glass or plastic substrate.

FIG. 1 illustrates an arrangement in which the cathode is disposed between the substrate and the anode. In other embodiments, the anode may be disposed between the cathode and the substrate.

The bulk heterojunction layer comprises a mixture of an electron acceptor and an electron donor. Optionally, the bulk heterojunction layer consists of the electron acceptor and the electron donor.

Each of the anode and cathode may independently be a single conductive layer or may comprise a plurality of layers.

The OPD may comprise layers other than the anode, cathode and bulk shown in FIG. 1. In some embodiments, a hole-transporting layer is disposed between the anode and the bulk heterojunction layer. In some embodiments, an electron-transporting layer is disposed between the cathode and the bulk heterojunction layer. In some embodiments, a work function modification layer is disposed between the bulk heterojunction layer and the anode, and/or between the bulk heterojunction layer and the cathode.

In use, the photodetectors as described in this disclosure may be connected to a voltage source for applying a reverse bias to the device and/or a device configured to measure photocurrent. The voltage applied to the photodetectors may be variable. In some embodiments, the photodetector may be continuously biased when in use.

In some embodiments, a photodetector system comprises a plurality of photodetectors as described herein, such as an image sensor of a camera.

In some embodiments, a sensor may comprise an OPD as described herein and a light source wherein the OPD is configured to receive light emitted from the light source. In some embodiments, the light from the light source may or may not be changed before reaching the OPD. For example, the light may be filtered, down-converted or up-converted before it reaches the OPD.

In some embodiments, the light source has a peak wavelength of greater than 750 nm, optionally greater than 900 nm, optionally less than 1500 nm.

The bulk heterojunction layer may contain an electron acceptor (n-type) compound of formula (I):

wherein EDG is an electron-donating group comprising a polycyclic heteroaromatic group and each EAG is an electron-accepting group of formula (II):

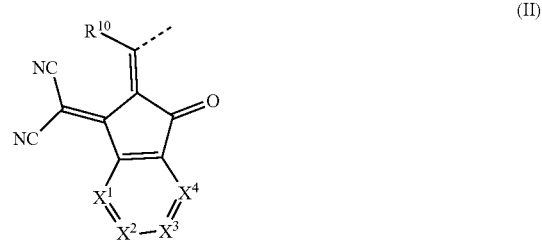

wherein $R^{10}$ in each occurrence is H or a substituent;
---- is a bond to EDG; and
each $X^1$-$X^4$ is independently $CR^{11}$ or N wherein $R^{11}$ in each occurrence is H or a substituent, with the proviso that at least one occurrence of at least one of $X^1$-$X^4$ is N.

Optionally, each $X^3$ is N.
Optionally, each $X^1$, $X^2$ and $X^4$ is $CR^{11}$.
Optionally, each $R^{11}$ is independently selected from H and $C_{1-12}$ alkyl.

Each EAG of formula (II) has a LUMO level that is deeper (i.e. further from vacuum) than that of EDG, preferably at least 1 eV deeper. The LUMO levels of EAG and EDG may be as determined by modelling the LUMO level of EAG-H and that of H-EDG-H, i.e. by replacing the bonds between EAG and EDG with bonds to a hydrogen atom. Modelling may be performed using Gaussian09 software available from Gaussian using Gaussian09 with B3LYP (functional) and LACVP* (Basis set).

Optionally, EDG comprises a fused heteroaromatic group containing at least one fused thiophene. Optionally, the fused heteroaromatic group comprises or consists of fused thiophene and one or both of benzene and cyclopentadiene groups, each of which may independently be unsubstituted or substituted with one or more substituents. Each thiophene is optionally unsubstituted or substituted with one or more groups $R^4$ other than H. Each benzene is optionally unsubstituted or substituted with one or more groups $R^3$ other than H. Each cyclopentadiene is optionally unsubstituted or substituted with one or more $R^1$ groups. $R^1$, $R^3$ and $R^4$ are as described below with reference to Formula (Ia).

Optionally, EDG is selected from:

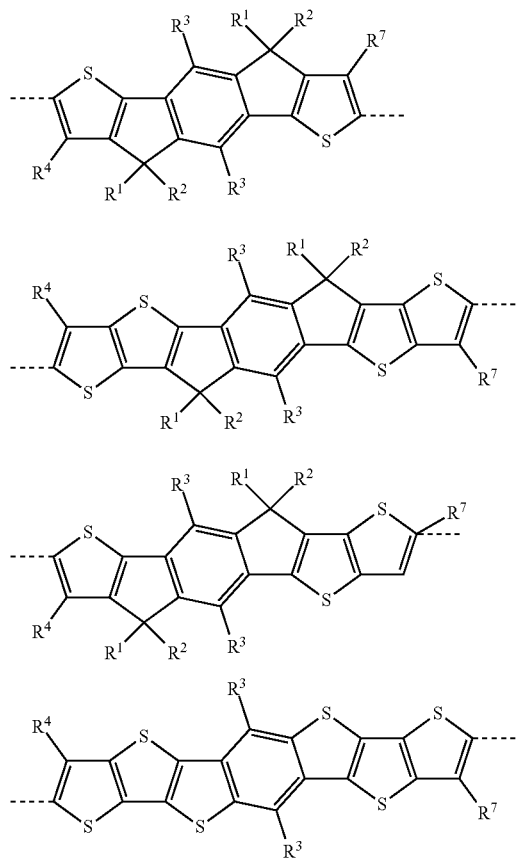

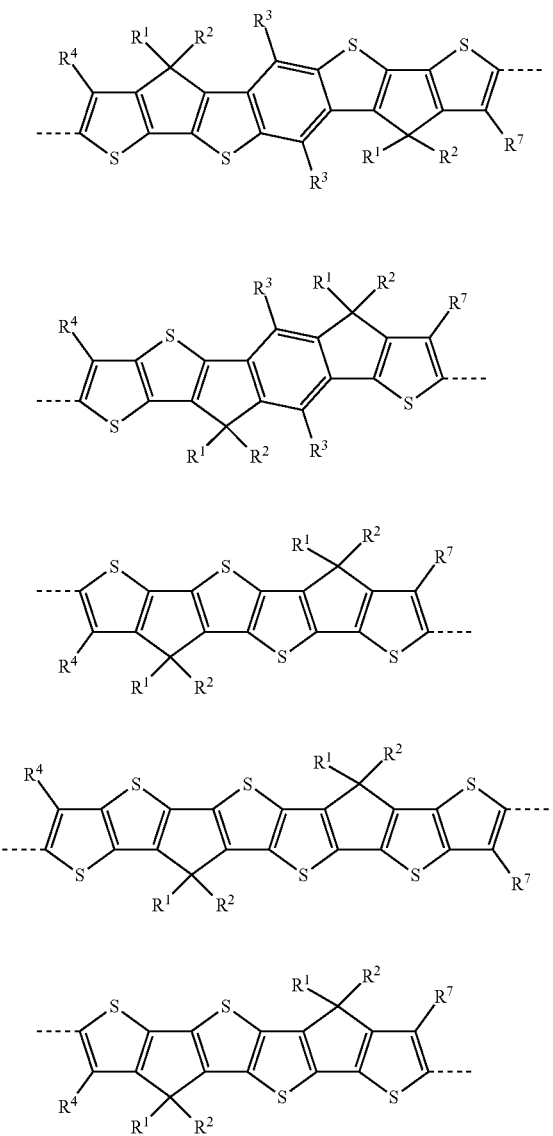

wherein $R^1$, $R^2$, $R^4$ and $R^7$ independently in each occurrence are as described below with reference to Formula (Ia).

Optionally, the compound of formula (I) has formula (Ia):

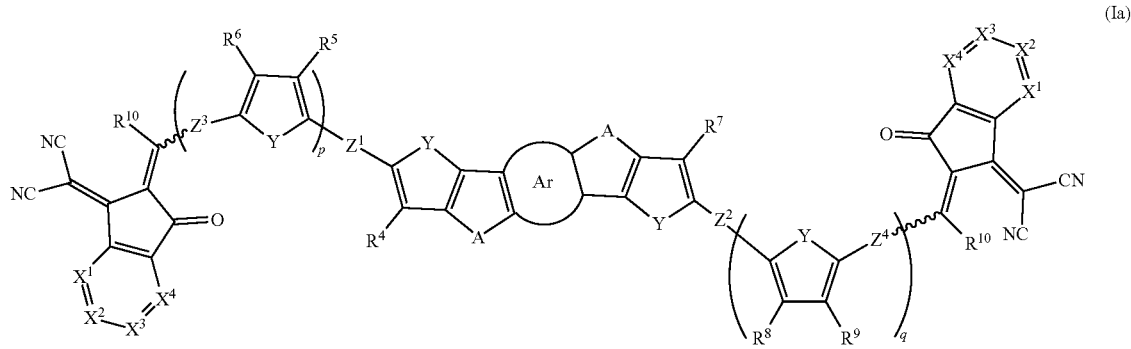

(Ia)

wherein:

Ar is furan, thiophene or benzene which is unsubstituted or substituted with one or more substituents;

each Y is independently O or S;

each A is independently O, S or $CR^1R^2$ wherein $R^1$ and $R^2$ independently in each occurrence is a substituent;

each $R^4$-$R^9$ is independently H or a substituent;

p is 0, 1, 2 or 3;

q is 0, 1, 2 or 3;

$Z^1$ is a direct bond or, together with $R^4$ or $R^5$, forms an aromatic or heteroaromatic group $Ar^1$;

$Z^2$ is a direct bond or, together with $R^2$ or $R^8$, forms an aromatic or heteroaromatic group $Ar^2$;

$Z^3$ is a direct bond or, together with $R^6$, forms an aromatic or heteroaromatic group $Ar^3$; and $Z^4$ is a direct bond or, together with $R^9$, forms an aromatic or heteroaromatic group $Ar^4$.

In some embodiments, each $Z^1$-$Z^4$ is a direct bond.

In embodiments where one or more of $Z^1$-$Z^4$ forms part of an aromatic or heteroaromatic group $Ar^1$-$Ar^4$, respectively, each $Ar^1$-$Ar^4$ (where present) is preferably a thiophene.

$Ar^1$-$Ar^4$ are each independently unsubstituted or substituted with one or more substituents. Optionally, substituents of $Ar^1$-$Ar^4$ are selected from $C_{1-12}$ alkyl wherein one or more non-adjacent, non-terminal C atoms may be replaced with O, S, COO or CO.

Optionally, the compound of formula (I) has formula (Ib):

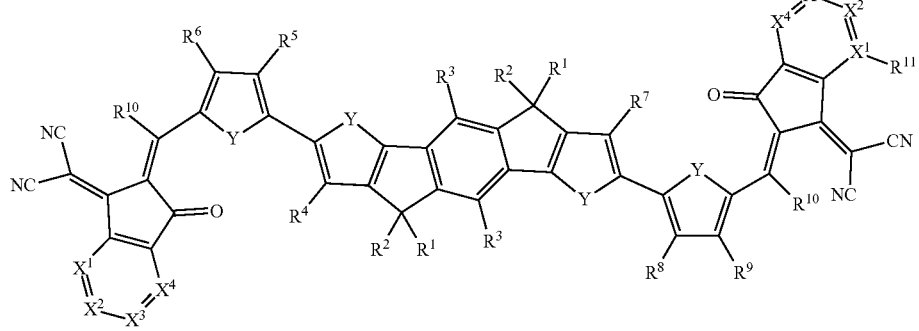

wherein each $R^3$ is, independently in each occurrence, H or a substituent.

Optionally, the compound of formula (I) has formula (Ic):

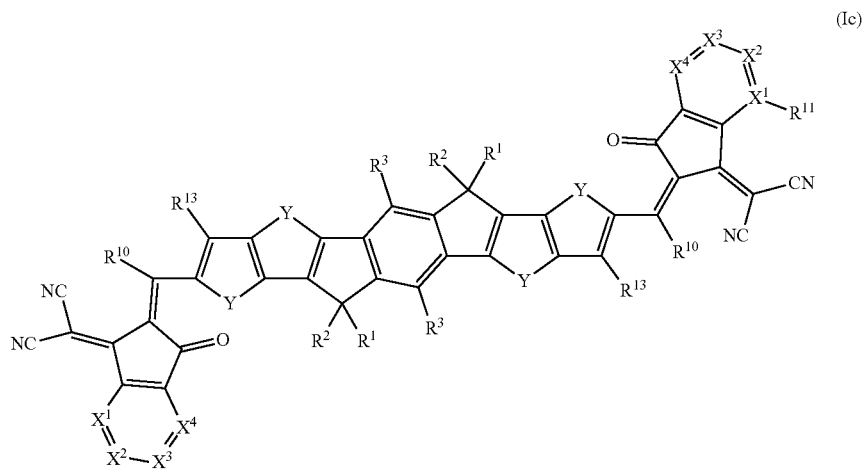

wherein $R^3$ in each occurrence is independently H or a substituent, optionally H or $C_{1-12}$ alkyl wherein one or more non-adjacent, non-terminal C atoms may be replaced with O, S, COO or CO.

Optionally, $R^1$ and $R^2$ of formula (Ia), (Ib) or (Ic) independently in each occurrence are selected from the group consisting of:

linear, branched or cyclic $C_{1-20}$ alkyl wherein one or more non-adjacent, non-terminal C atoms may be replaced by O, S, $NR^{12}$, CO or COO wherein $R^{12}$ is a $C_{1-12}$ hydrocarbyl and one or more H atoms of the $C_{1-20}$ alkyl may be replaced with F; and a group of formula $(Ak)u-(Ar^6)v$ wherein Ak is a $C_{1-12}$ alkylene chain in which one or more C atoms may be replaced with O, S, CO or COO; u is 0 or 1; $Ar^6$ in each occurrence is independently an aromatic or heteroaromatic group which is unsubstituted or substituted with one or more substituents; and v is at least 1, optionally 1, 2 or 3.

$Ar^6$ is preferably phenyl.

Where present, substituents of $Ar^6$ may be a substituent $R^{14}$ wherein $R^{14}$ in each occurrence is independently selected from $C_{1-20}$ alkyl wherein one or more non-adjacent, non-terminal C atoms may be replaced by O, S, $NR^{12}$, CO or COO and one or more H atoms of the $C_{1-20}$ alkyl may be replaced with F.

A hydrocarbyl group as described anywhere herein is optionally selected from $C_{1-20}$ alkyl; unsubstituted phenyl; and phenyl substituted with one or more $C_{1-12}$ alkyl groups.

If v is 3 or more then $—(Ar^6)v$ may be a linear or branched chain of $Ar^6$ groups. A linear chain of $Ar^6$ groups as described herein has only on monovalent terminal $Ar^6$ group whereas a branched chain of $Ar^6$ groups has at least two monovalent terminal $Ar^6$ groups.

Optionally, at least one of $R^1$ and $R^2$ in each occurrence, optionally each R and $R^2$, is phenyl which is unsubstituted or substituted with one or more substituents selected from $R^{14}$ as described above.

Optionally, each $R^4$-$R^9$ of formula (Ia) or (Ib) is independently selected from:

H;

$C_{1-12}$ alkyl wherein one or more non-adjacent, non-terminal C atoms may be replaced with O, S, COO or CO; and an aromatic or heteroaromatic group $Ar^5$ which is unsubstituted or substituted with one or more substituents.

Optionally, each $R^3$ of formula (Ib) independently in each occurrence is selected from:

H;

$C_{1-12}$ alkyl wherein one or more non-adjacent, non-terminal C atoms may be replaced with O, S, COO or CO; and an aromatic or heteroaromatic group $Ar^5$ which is unsubstituted or substituted with one or more substituents.

$Ar^5$ is preferably an aromatic group, more preferably phenyl.

The one or more substituents of $Ar^5$, if present, may be selected from $C_{1-12}$ alkyl wherein one or more non-adjacent, non-terminal C atoms may be replaced with O, S, COO or CO.

In some embodiments, each $R^3$-$R^{10}$ is H; $C_{1-20}$ alkyl; or $C_{1-20}$ alkoxy.

In some embodiments at least one of, optionally both of, $R^5$ and $R^8$ is not H, and each $R^3$, $R^4$ and $R^6$-$R^{10}$ is H.

By "non-terminal" C atom of an alkyl group as used herein is meant a C atom of the alkyl other than the methyl C atom of a linear (n-alkyl) chain or the methyl C atoms of a branched alkyl chain.

Exemplary compounds of formula (I) are:

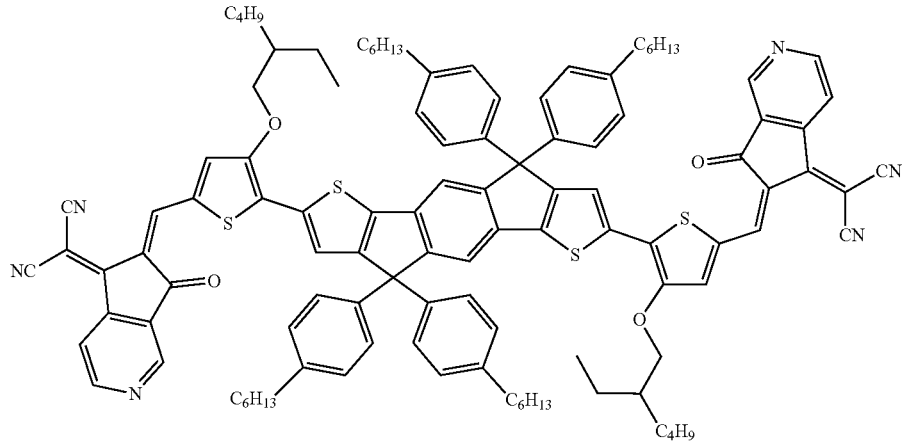

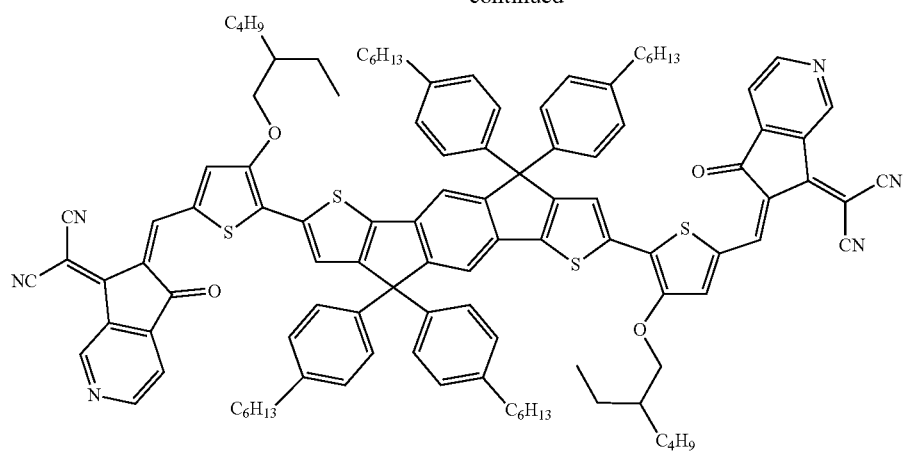
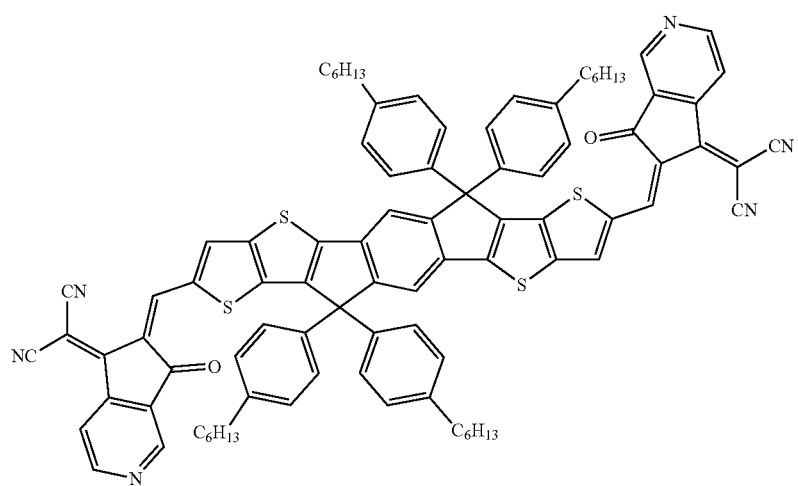
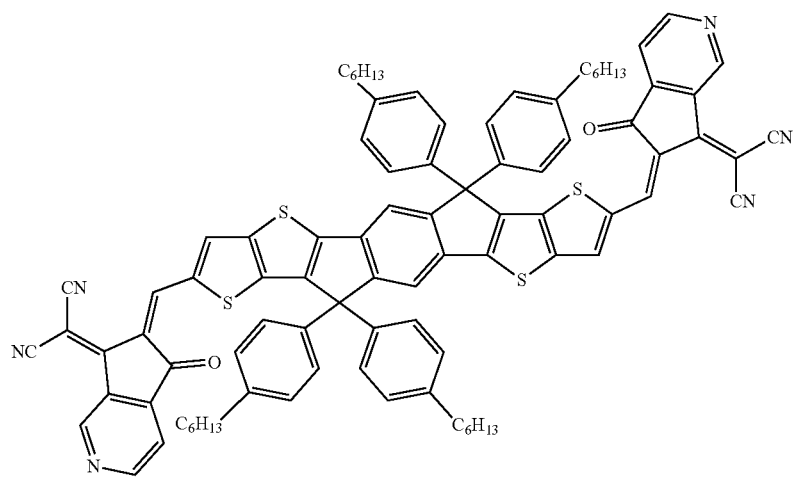

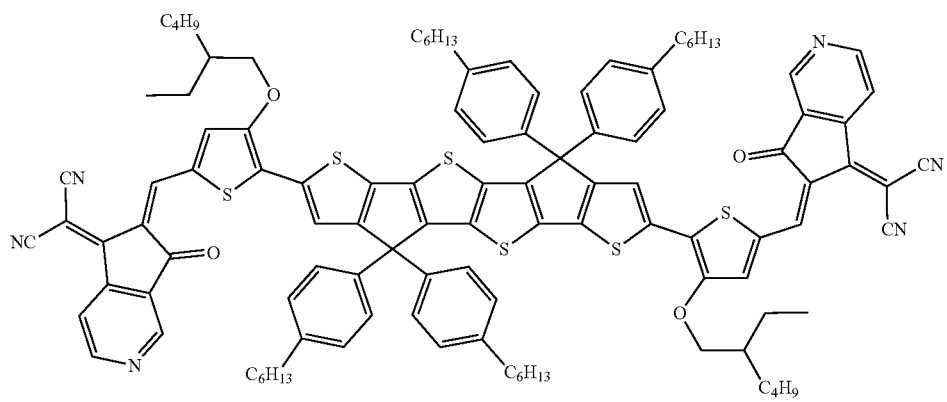
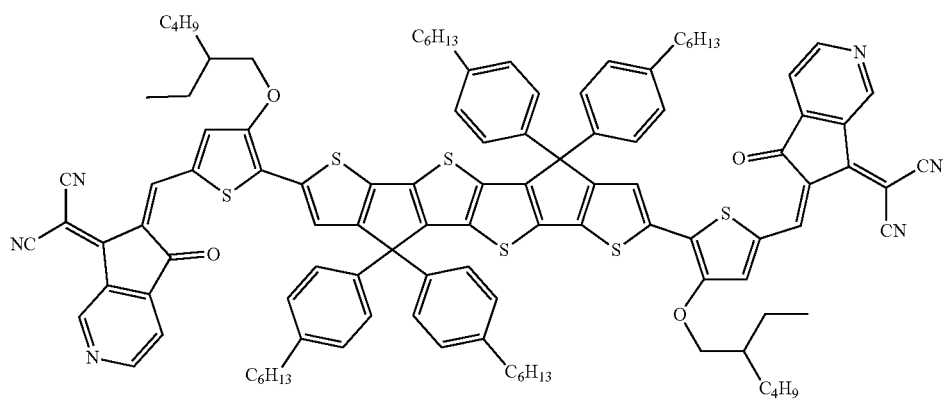
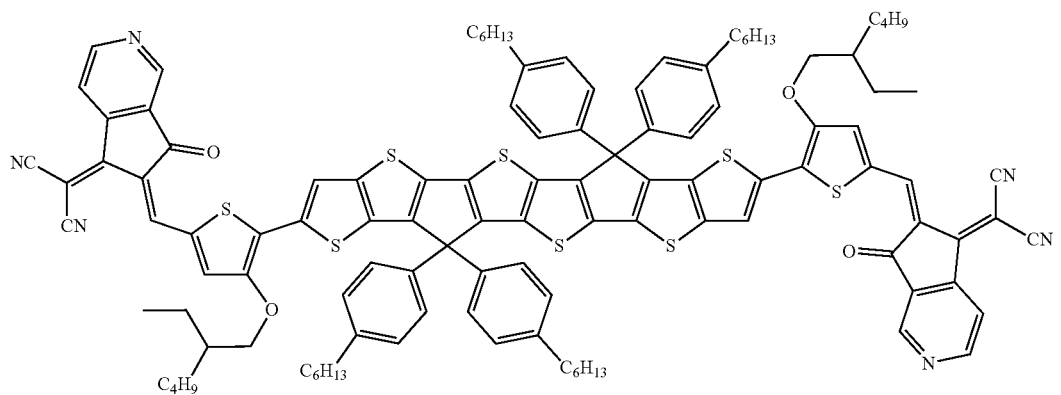
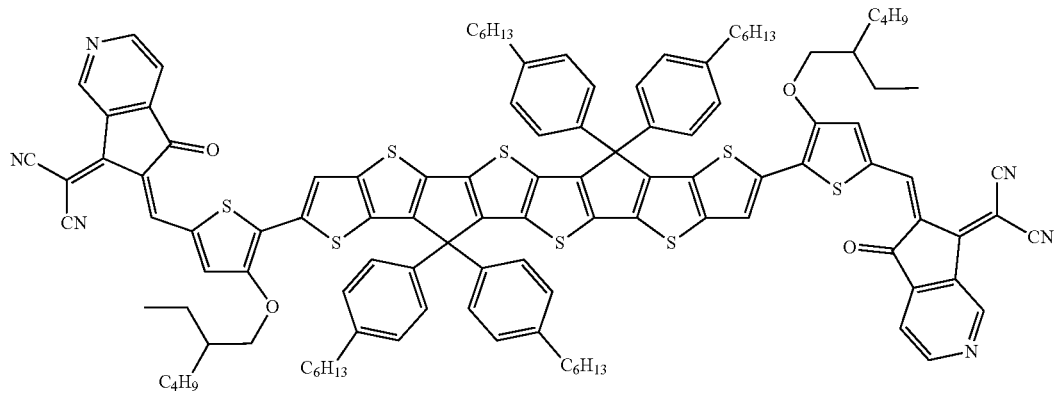

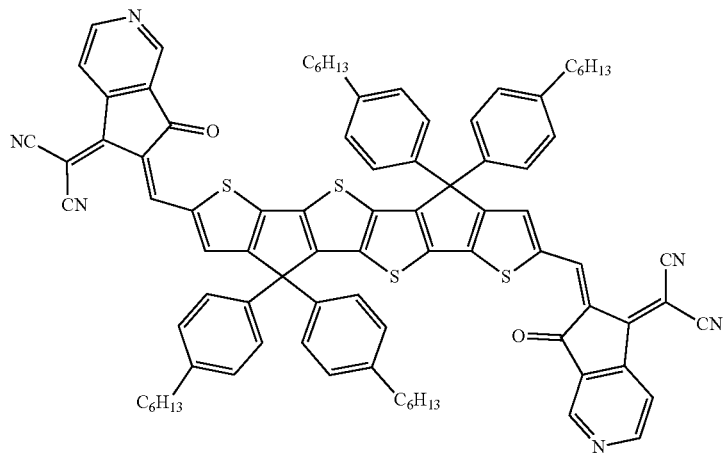
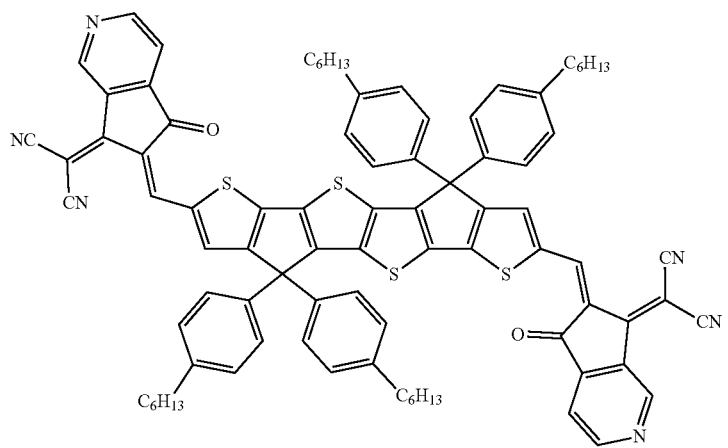
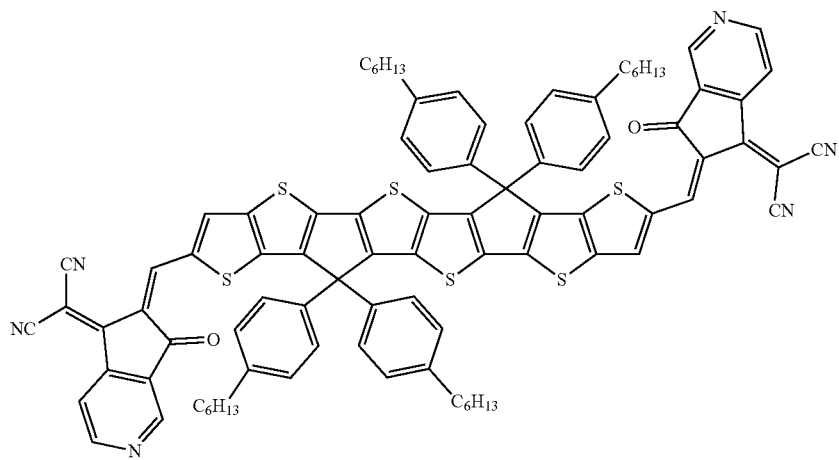

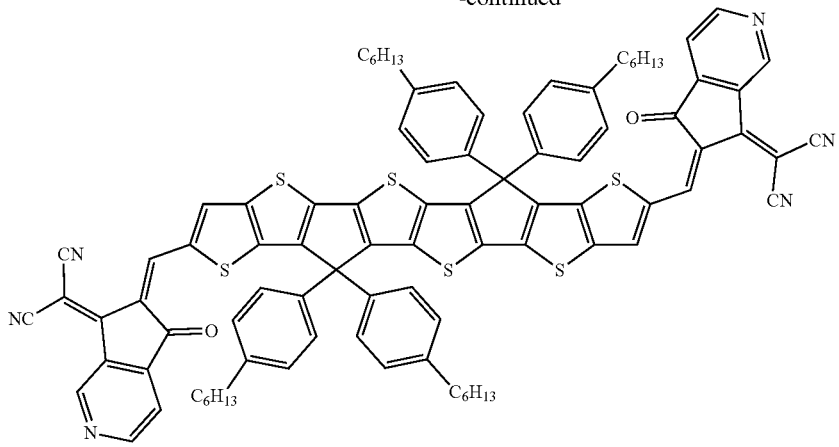

The compound of formula (I) may be used in combination with a fullerene acceptor.

The compound of formula (I):fullerene acceptor weight ratio may be in the range of about 1:0.1-1:1, preferably in the range of about 1:0.1-1:0.5.

The fullerene may be a $C_{60}$, $C_{70}$, $C_{76}$, $C_{78}$ or $C_{84}$ fullerene or a derivative thereof including, without limitation, PCBM-type fullerene derivatives (including phenyl-C61-butyric acid methyl ester ($C_{60}$PCBM) and phenyl-C71-butyric acid methyl ester ($C_{70}$PCBM)), TCBM-type fullerene derivatives (e.g. tolyl-C61-butyric acid methyl ester ($C_{60}$TCBM)), and ThCBM-type fullerene derivatives (e.g. thienyl-C61-butyric acid methyl ester ($C_{60}$ThCBM)

Where present, a fullerene acceptor may have formula (III):

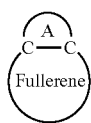

(III)

wherein A, together with the C-C group of the fullerene, forms a monocyclic or fused ring group which may be unsubstituted or substituted with one or more substituents.

Exemplary fullerene derivatives include formulae (IIIa), (IIIb) and (IIIc):

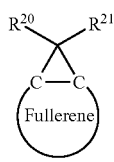

(IIIa)

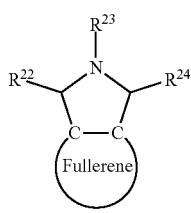

(IIIb)

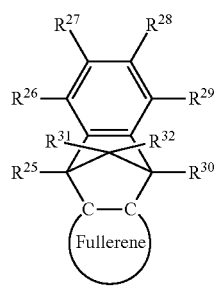

(IIIc)

wherein $R^{20}$-$R^{32}$ are each independently H or a substituent.

Substituents $R^{20}$-$R^{32}$ are optionally and independently in each occurrence selected from the group consisting of aryl or heteroaryl, optionally phenyl, which may be unsubstituted or substituted with one or more substituents; and $C_{1-20}$ alkyl wherein one or more non-adjacent, non-terminal C atoms may be replaced with O, S, CO or COO and one or more H atoms may be replaced with F.

Substituents of aryl or heteroaryl groups $R^{20}$-$R^{32}$, where present, are optionally selected from $C_{1-12}$ alkyl wherein one or more non-adjacent, non-terminal C atoms may be replaced with O, S, CO or COO and one or more H atoms may be replaced with F.

The donor (p-type) compound is not particularly limited and may be appropriately selected from electron donating materials that are known to the person skilled in the art, including organic polymers and non-polymeric organic molecules. The p-type compound has a HOMO deeper (further from vacuum) than a LUMO of the compound of formula (I). Optionally, the gap between the HOMO level of the p-type donor and the LUMO level of the n-type acceptor compound of formula (I) is less than 1.4 eV.

In a preferred embodiment the p-type donor compound is an organic conjugated polymer, which can be a homopolymer or copolymer including alternating, random or block copolymers. Preferred are non-crystalline or semi-crystalline conjugated organic polymers. Further preferably the p-type organic semiconductor is a conjugated organic polymer with a low bandgap, typically between 2.5 eV and 1.5 eV, preferably between 2.3 eV and 1.8 eV.

Optionally, the p-type donor has a HOMO level no more than 5.5 eV from vacuum level. Optionally, the p-type donor has a HOMO level at least 4.1 eV from vacuum level.

As exemplary p-type donor polymers, polymers selected from conjugated hydrocarbon or heterocyclic polymers including polyacene, polyaniline, polyazulene, polybenzofuran, polyfluorene, polyfuran, polyindenofluorene, polyindole, polyphenylene, polypyrazoline, polypyrene, polypyridazine, polypyridine, polytriarylamine, poly(phenylene vinylene), poly(3-substituted thiophene), poly(3,4-bisubstituted thiophene), polyselenophene, poly(3-substituted selenophene), poly(3,4-bisubstituted selenophene), poly(bisthiophene), poly(terthiophene), poly(bisselenophene), poly(terselenophene), polythieno[2,3-b]thiophene, polythieno[3,2-b]thiophene, polybenzothiophene, polybenzo[1,2-b:4,5-b']dithiophene, polyisothianaphthene, poly(monosubstituted pyrrole), poly(3,4-bisubstituted pyrrole), poly-1,3,4-oxadiazoles, polyisothianaphthene, derivatives and co-polymers thereof may be mentioned. Preferred examples of p-type donors are copolymers of polyfluorenes and polythiophenes, each of which may be substituted, and polymers comprising benzothiadiazole-based and thiophene-based repeating units, each of which may be substituted. It is understood that the p-type donor may also consist of a mixture of a plurality of electron donating materials.

Optionally, the donor polymer comprises a repeat unit of formula (IV):

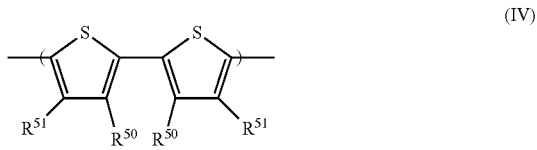

(IV)

wherein $R^{50}$ and $R^{51}$ independently in each occurrence is H or a substituent.

Substituents $R^{50}$ and $R^{51}$ may be selected from groups other than H described with respect to $R^4$ and $R^7$.

Preferably, each $R^{50}$ is a substituent. In a preferred embodiment, the $R^{50}$ groups are linked to form a group of formula —$Z^1$—$C(R^{52})_2$— wherein $Z^1$ is O, $NR^5$, or $C(R^{52})_2$; $R^{52}$ in each occurrence is H or a substituent, preferably a substituent as described with reference to $R^1$, most preferably a $C_{1-30}$ hydrocarbyl group; and $R^{53}$ is a substituent, preferably a $C_{1-30}$ hydrocarbyl group.

Preferably, each $R^{51}$ is H.

Optionally, the donor polymer comprises a repeat unit of formula (V):

(V)

wherein $R^{54}$ in each occurrence is independently H or a substituent. Optionally, substituents $R^{54}$ are selected from the group consisting of F, CN, $NO_2$, and $C_{1-20}$ alkyl wherein one or more non-adjacent, non-terminal C atoms may be replaced with O, S, CO or COO and one or more H atoms may be replaced with F.

In some embodiments, the weight of the donor compound to the acceptor compound is from about 1:0.5 to about 1:2.

Preferably, the weight ratio of the donor compound to the acceptor compound is about 1:1 or about 1:1.5.

At least one of the first and second electrodes is transparent so that light incident on the device may reach the bulk heterojunction layer. In some embodiments, both of the first and second electrodes are transparent.

Each transparent electrode preferably has a transmittance of at least 70%, optionally at least 80%, to wavelengths in the range of 300-900 nm.

In some embodiments, one electrode is transparent and the other electrode is reflective.

Optionally, the transparent electrode comprises or consists of a layer of transparent conducting oxide, preferably indium tin oxide or indium zinc oxide. In preferred embodiments, the electrode may comprise poly 3,4-ethylenedioxythiophene (PEDOT). In other preferred embodiments, the electrode may comprise a mixture of PEDOT and polystyrene sulfonate (PSS). The electrode may consist of a layer of PEDOT:PSS.

Optionally, the reflective electrode may comprise a layer of a reflective metal. The layer of reflective material may be aluminium or silver or gold. In some embodiments, a bi-layer electrode may be used. For example, the electrode may be an indium tin oxide (ITO)/silver bi-layer, an ITO/aluminium bi-layer or an ITO/gold bi-layer.

The device may be formed by forming the bulk heterojunction layer over one of the anode and cathode supported by a substrate and depositing the other of the anode or cathode over the bulk heterojunction layer.

The area of the OPD may be less than about 3 cm$^2$, less than about 2 cm$^2$, less than about 1 cm$^2$, less than about 0.75 cm$^2$, less than about 0.5 cm$^2$ or less than about 0.25 cm$^2$. The substrate may be, without limitation, a glass or plastic substrate. The substrate can be described as an inorganic semiconductor. In some embodiments, the substrate may be silicon. For example, the substrate can be a wafer of silicon. The substrate is transparent if, in use, incident light is to be transmitted through the substrate and the electrode supported by the substrate.

The substrate supporting one of the anode and cathode may or may not be transparent if, in use, incident light is to be transmitted through the other of the anode and cathode.

The bulk heterojunction layer may be formed by any process including, without limitation, thermal evaporation and solution deposition methods.

Preferably, the bulk heterojunction layer is formed by depositing a formulation comprising the acceptor material and the electron donor material dissolved or dispersed in a solvent or a mixture of two or more solvents. The formulation may be deposited by any coating or printing method including, without limitation, spin-coating, dip-coating, roll-coating, spray coating, doctor blade coating, wire bar coating, slit coating, ink jet printing, screen printing, gravure printing and flexographic printing.

The one or more solvents of the formulation may optionally comprise or consist of benzene substituted with one or more substituents selected from chlorine, $C_{1-10}$ alkyl and $C_{1-10}$ alkoxy wherein two or more substituents may be linked to form a ring which may be unsubstituted or substituted with one or more $C_{1-6}$ alkyl groups, optionally toluene, xylenes, trimethylbenzenes, tetramethylbenzenes, anisole, indane and its alkyl-substituted derivatives, and tetralin and its alkyl-substituted derivatives.

The formulation may comprise a mixture of two or more solvents, preferably a mixture comprising at least one benzene substituted with one or more substituents as described above and one or more further solvents. The one or more further solvents may be selected from esters, optionally alkyl or aryl esters of alkyl or aryl carboxylic acids, optionally a $C_{1-10}$ alkyl benzoate, benzyl benzoate or dimethoxybenzene. In preferred embodiments, a mixture of trimethylbenzene and benzyl benzoate is used as the solvent. In other preferred embodiments, a mixture of trimethylbenzene and dimethoxybenzene is used as the solvent.

The formulation may comprise further components in addition to the electron acceptor, the electron donor and the one or more solvents. As examples of such components, adhesive agents, defoaming agents, deaerators, viscosity enhancers, diluents, auxiliaries, flow improvers colourants, dyes or pigments, sensitizers, stabilizers, nanoparticles, surface-active compounds, lubricating agents, wetting agents, dispersing agents and inhibitors may be mentioned.

The organic photodetector as described herein may be used in a wide range of applications including, without limitation, detecting the presence and/or brightness of ambient light and in a sensor comprising the organic photodetector and a light source.

The photodetector may be configured such that light emitted from the light source is incident on the photodetector and changes in wavelength and/or brightness of the light may be detected, e.g. due to absorption by and/or emission of light from a target material in a sample disposed in a light path between the light source and the organic photodetector. The sensor may be, without limitation, a gas sensor, a biosensor, an X-ray imaging device, an image sensor such as a camera image sensor, a motion sensor (for example for use in security applications) a proximity sensor or a fingerprint sensor. A 1D or 2D photosensor array may comprise a plurality of photodetectors as described herein in an image sensor. The photodetector may be configured to detect light emitted from a target analyte which emits light upon irradiation by the light source or which is bound to a luminescent tag which emits light upon irradiation by the light source. The photodetector may be configured to detect a wavelength of light emitted by the target analyte or a luminescent tag bound thereto.

EXAMPLES

Synthesis

An electron-acceptor group precursor (mixture of isomers) was prepared according to the following reaction scheme:

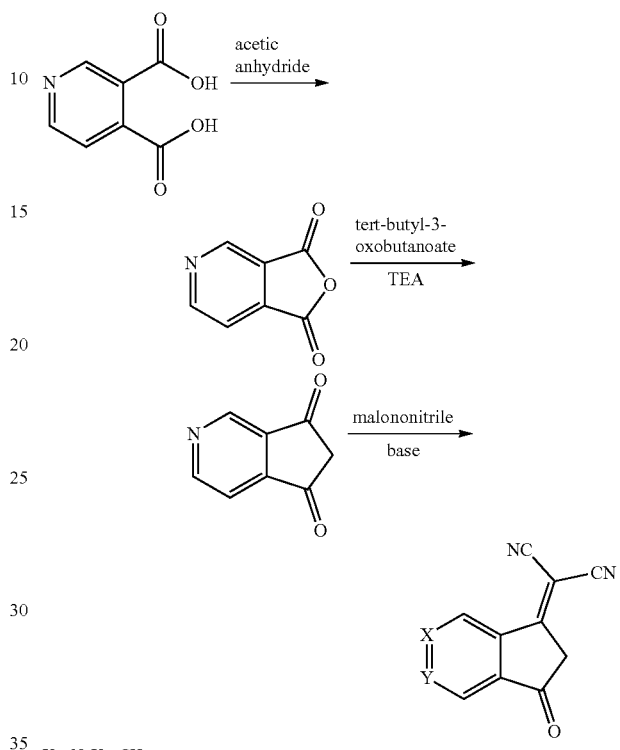

X = N, Y = CH
X = CH, Y = N

Compound Example 1 was formed by reaction of the electron-acceptor group precursor according to the following reaction scheme:

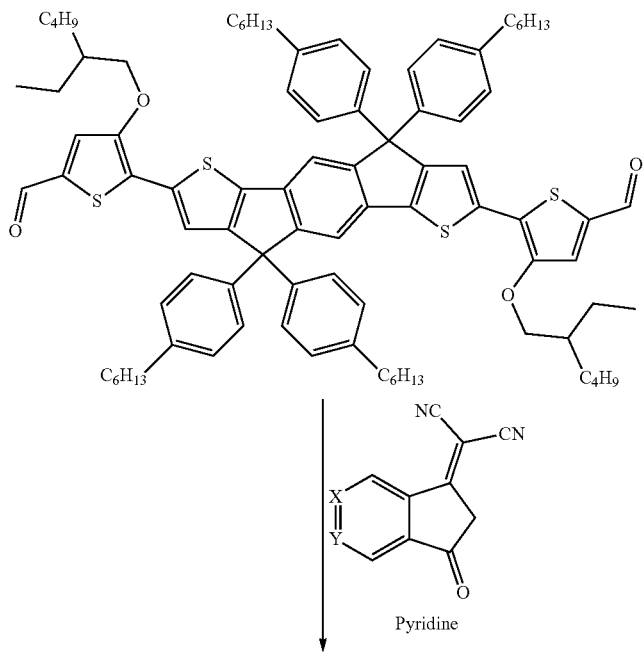

-continued

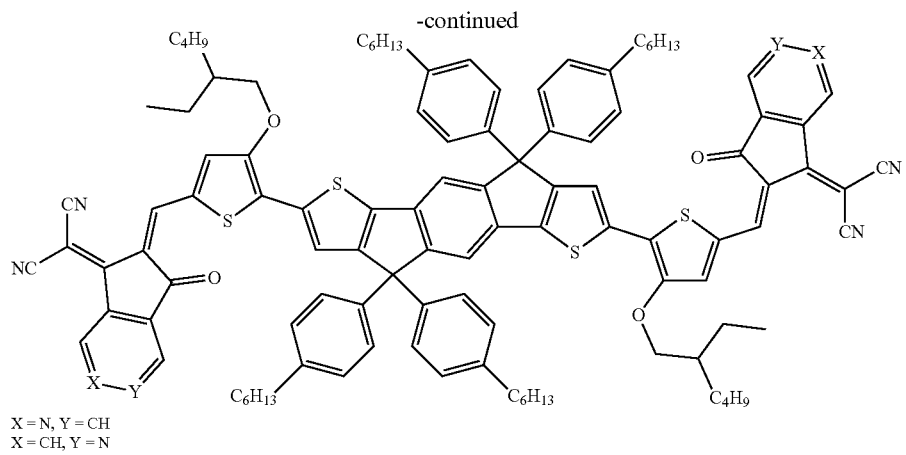

X = N, Y = CH
X = CH, Y = N

Step 1 & 2

Pyridine-3,4-dicarboxylic acid (10 g, 59.8 mmol) was refluxed in acetic anhydride (70 mL) under nitrogen atmosphere for 30 mins. After cooling, trimethylamine (16.5 mL, 119 mmol) was added dropwise followed by tert-butyl 3-oxobutanoate (9.46 g, 59.8 mmol) and the reaction mixture was stirred at room temperature for 18 h. The volatiles were removed leave a crude material. The crude material was purified by column chromatography on silica eluting with 10% methanol in DCM to yield 12 g of a gummy solid. The material was dissolved in water and cooled in an ice bath. 1.5 N HCl (100 mL) and conc HCl (5 mL) was added to acidify the mixture to pH 2-3. A brown precipitate was formed and isolated by filtration. The solid was triturated with acetone twice and then filtered and dried. 5 g of this material was recrystallized from acetonitrile and placed in the freezer overnight yielding 2.9 g of crude bis-ketone.

Step 3

Malononitrile (7.79 g, 118 mmol) was dissolved in ethanol (300 mL) under nitrogen atmosphere. Sodium acetate (8.07 g, 98.4 mmol) was added and the mixture was stirred for 1 h at room temperature. The crude stage 2 material (2.9 g) was added portion-wise to the mixture and stirred for 16 h. The reaction mixture was concentrated and the crude was taken in acetone (300 mL) and stirred for 4 h. The solid was removed by filtration and the filtrate was concentrated to obtain 12 g of crude. The crude was purified by reverse phase column chromatography eluting with 10% acetonitrile in water. The product-containing fractions were concentrated and placed in the freezer to obtain 600 mg. The product was suspended in 1.5N HCl (25 mL) and placed in a freeze dryer. Upon completion it was used in the next step without further purification.

Step 4

The thiophene core (400 mg, 288 µmol) and stage 3 material (562 mg, 115 µmol) were dissolved in chloroform under nitrogen atmosphere. Pyridine (5 mL) was added and the reaction was stirred at 65° C. for 65 h. After cooling the solvents were removed and the crude residue was purified by column chromatography on silica eluting with 2% methanol in chloroform. The product-containing fractions were concentrated and triturated with acetonitrile for 3 h. After filtration the solid was precipitated from DCM/hexanes (3/30 mL) twice and the solid was filtered and dried to give 495 mg of product. LCMS showed a purity of 98.31%.

Modelling Data

LUMO levels and HOMO-LUMO bandgaps of compounds of formula (Ib) were modelled in which $R^1$, $R^2$, $R^5$ and $R^8$ are each methyl; $R^3$, $R^4$, $R^6$, $R^7$, $R^9$ and $R^{10}$ are each H; and $X^1$-$X^4$ are as in Table 1.

For comparison, compounds in which $X^1$-$X^4$ groups of formula (Ib) are either C—H or C—F replaced with F were also modelled.

Quantum chemical modelling was performed using Gaussian09 software available from Gaussian using Gaussian09 with B3LYP (functional) and LACVP* (Basis set).

TABLE 1

| Compound | $X^1$ | $X^2$ | $X^3$ | $X^4$ | LUMO (eV) | Band gap (eV) |
|---|---|---|---|---|---|---|
| Model Comparative Compound 1 | CH | CH | CH | CH | 3.26 | 1.77 |
| Model Comparative Compound 2 | CH | CF | CH | CH | 3.36 | 1.73 |
| Model Comparative Compound 3 | CH | CF | CF | CH | 3.39 | 1.74 |
| Model Compound Example 1 | CH | CH | N | CH | 3.50 | 1.69 |
| Model Compound Example 2 | CH | N | CH | CH | 3.46 | 1.75 |

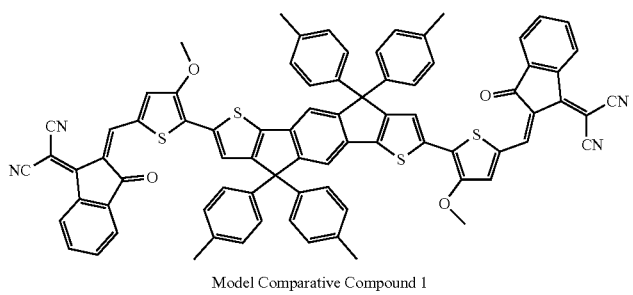 [SMILES: COc1cc(/C=C2\C(=O)c3ccccc3C2=C(C#N)C#N)sc1-c1cc2c(s1)-c1cc3c(cc1C2(c1ccc(C)cc1)c1ccc(C)cc1)-c1sc(-c2sc(/C=C4\C(=O)c5ccccc5C4=C(C#N)C#N)cc2OC)cc1C3(c1ccc(C)cc1)c1ccc(C)cc1]

Model Comparative Compound 1

TABLE 1-continued
| Compound | X¹ | X² | X³ | X⁴ | LUMO (eV) | Band gap (eV) |
|---|---|---|---|---|---|---|
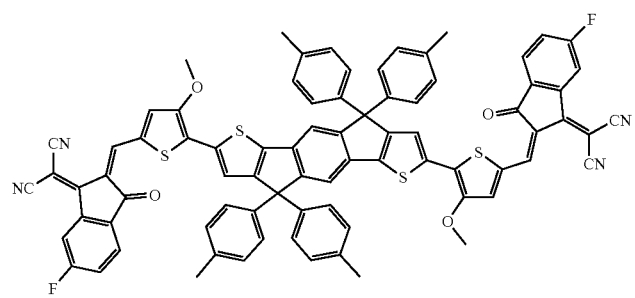
Model Comparative Compound 2
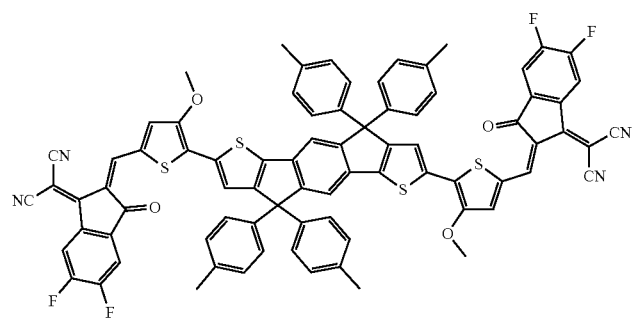
Model Comparative Compound 3
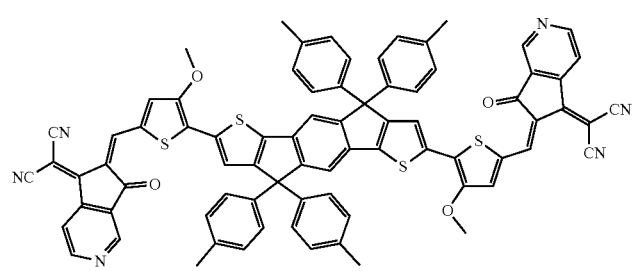
Model Compound Example 1
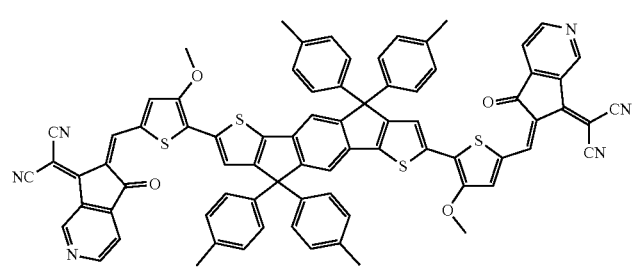
Model Compound Example 2

With reference to Table 1, Model Compound Examples 1 and 2 have a LUMO which is deeper (i.e. further from vacuum level) and a similar or smaller band gap than Model Comparative Compounds 1-3.

Absorption

Figure 2:
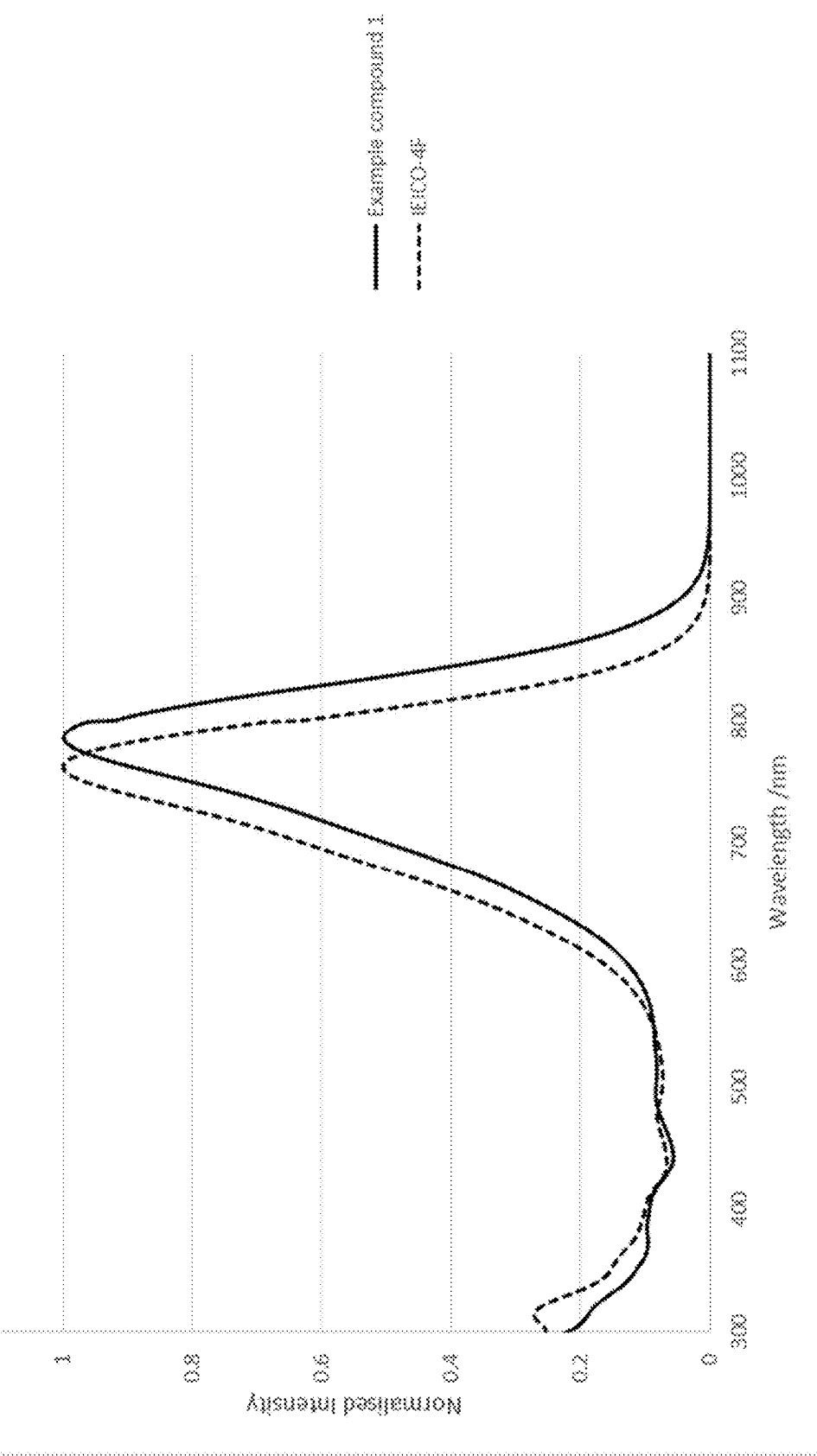
FIG. 2 illustrates absorption spectra for a compound according to some embodiments of the present disclosure and a comparative compound.

FIG. 2 shows absorption spectra for Compound Example 1 and comparative compound IEICO-4F. Compound Example 1 has a significantly longer peak wavelength (786 nm) than IEICO-4F (762 nm).

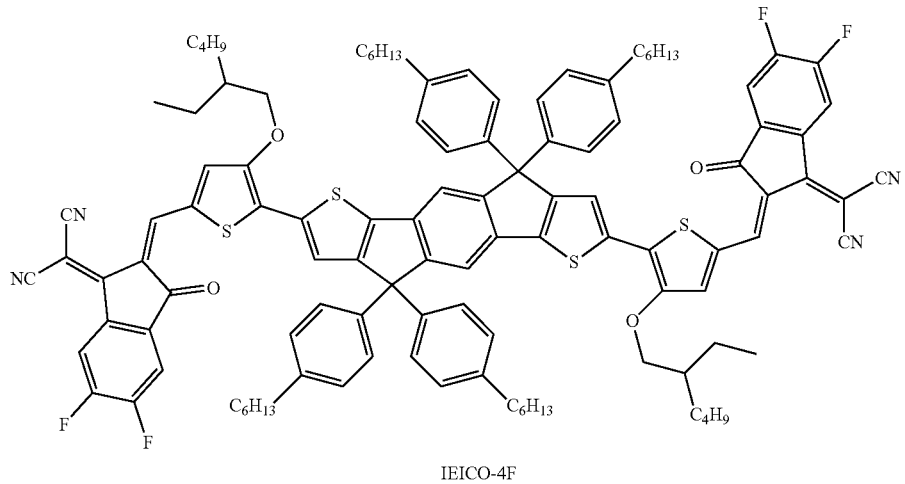

IEICO-4F

HOMO and LUMO Energy Levels

HOMO and LUMO levels of films of Compound Example 1 and comparative compound IEICO-4F were determined by square wave voltammetry (SWV) and the results are set out in Table 2.

The LUMO level of Compound Example 1 is deeper and its HOMO-LUMO gap is smaller as compared to comparative compound IEICO-4F having a structure of Compound Example 1 except that each $X^2$ and $X^3$ is CF.

TABLE 2

|  | Film HOMO/eV | Film LUMO/eV | HOMO-LUMO gap (eV) |
|---|---|---|---|
| Compound Example 1 | −5.45 | −4.07 | 1.38 |
| IEICO-4F (comparative) | −5.45 | −4.03 | 1.42 |

The HOMO and LUMO energy levels of compounds reported herein were determined from films of the compounds using SWV at room temperature. In SWV, the current at a working electrode is measured while the potential between the working electrode and a reference electrode is swept linearly in time. The difference current between a forward and reverse pulse is plotted as a function of potential to yield a voltammogram. The apparatus to measure HOMO or LUMO energy levels by SWV may comprise a cell containing tertiary butyl ammonium perchlorate or tertiary butyl ammonium hexafluorophosphate in acetonitrile; a glassy carbon working electrode; a platinum counter electrode and a leak free Ag/AgCl reference electrode.

Ferrocene is added directly to the existing cell at the end of the experiment for calculation purposes where the potentials are determined for the oxidation and reduction of ferrocene versus Ag/AgCl using cyclic voltammetry (CV).

Apparatus:
CHI 660D Potentiostat.
3 mm Diameter glassy carbon working electrode
Leak free Ag/AgCl reference electrode
Pt wire auxiliary or counter electrode.
0.1 M Tetrabutylammonium hexafluorophosphate in acetonitrile.

Method:
The sample is dissolved in toluene (3 mg/ml) and spun at 3000 rpm directly on to the glassy carbon working electrode.

LUMO=4.8−$E$ ferrocene (peak to peak average)−$E$ reduction of sample (peak maximum).

HOMO=4.8−$E$ ferrocene (peak to peak average)+$E$ oxidation of sample (peak maximum).

A typical SWV experiment runs at 15 Hz frequency; 25 mV amplitude and 0.004 V increment steps. Results are calculated from 3 freshly spun film samples for both the HOMO and LUMO data.

All experiments are run under an Argon gas purge.

The invention claimed is:

1. A compound of formula (Ia):

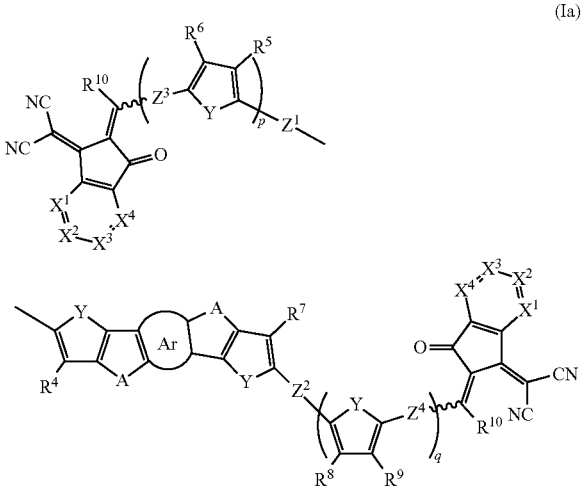

wherein:
Ar is furan, thiophene, thienothiophene, or benzene, which is unsubstituted or substituted with one or more substituents;
each Y is independently O or S;
each A is independently O, S, or $CR^1R^2$, wherein $R^1$ and $R^2$ independently in each occurrence is a substituent;
each $R^4$-$R^9$ is independently H or a substituent;
p is 0, 1, 2, or 3;
q is 0, 1, 2, or 3;
$Z^1$ is a direct bond or, together with $R^4$ or $R^5$, forms an aromatic or heteroaromatic group $Ar^1$;
$Z^2$ is a direct bond or, together with $R^7$ or $R^8$, forms an aromatic or heteroaromatic group $Ar^2$;
$Z^3$ is a direct bond or, together with $R^6$, forms an aromatic or heteroaromatic group $Ar^3$;
$Z^4$ is a direct bond or, together with $R^9$, forms an aromatic or heteroaromatic group $Ar^4$;
$R^{10}$ in each occurrence is H or a substituent; and
each $X^1$-$X^4$ is independently $CR^{11}$ or N, wherein $R^{11}$ in each occurrence is H or a substituent, with the proviso that at least one occurrence of at least one of $X^1$-$X^4$ is N.

2. The compound according to claim 1 wherein each $X^3$ is N.

3. The compound according to claim 2 wherein each $X^1$, $X^2$ and $X^4$ is $CR^{11}$.

4. The compound according to claim 1 wherein each $R^{11}$ is independently selected from H and $C_{1-12}$ alkyl.

5. The compound according to claim 1 wherein the compound has formula (Ib):

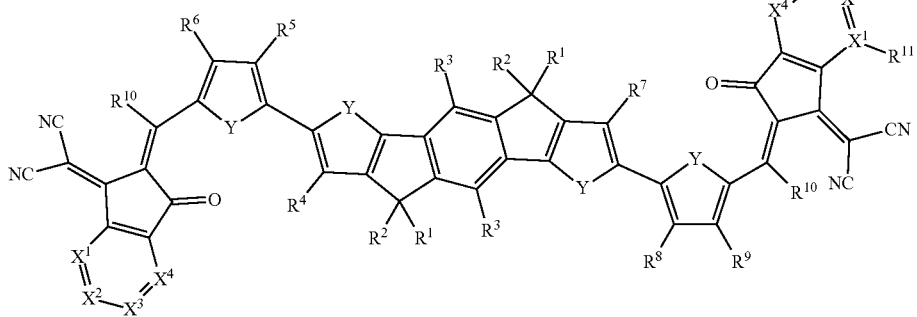

(Ib)

wherein each $R^3$ is, independently in each occurrence, H or a substituent.

6. The compound according to claim 1, wherein $R^1$ and $R^2$ independently in each occurrence are selected from the group consisting of:
linear, branched or cyclic $C_{1-20}$ alkyl, wherein one or more non-adjacent, non-terminal C atoms may be replaced by O, S, NR12, CO or COO, wherein $R^{12}$ is a $C_{1-12}$ hydrocarbyl and one or more H atoms of the $C_{1-20}$ alkyl may be replaced with F; and
a group of formula $(Ak)u-(Ar^6)v$, wherein Ak is a $C_{1-12}$ alkylene chain in which one or more C atoms may be replaced with O, S, CO or COO; u is 0 or 1; $Ar^6$ in each occurrence is independently an aromatic or heteroaromatic group, which is unsubstituted or substituted with one or more substituents; and v is at least 1.

7. The compound according to claim 6, wherein at least one of $R^1$ and $R^2$ is phenyl which is unsubstituted or substituted with one or more substituents selected from C1-20 alkyl, wherein one or more non-adjacent, non-terminal C atoms may be replaced by O, S, $NR^{12}$, CO or COO, and one or more H atoms of the $C_{1-20}$ alkyl may be replaced with F.

8. The compound according to claim 1 wherein each $R^4$-$R^9$ is independently selected from:
H;
$C_{1-12}$ alkyl, wherein one or more non-adjacent, non-terminal C atoms may be replaced with O, S, COO or CO; and
an aromatic or heteroaromatic group $Ar^5$ which is unsubstituted or substituted with one or more substituents.

9. The compound according to claim 5 wherein each $R^3$ independently in each occurrence is selected from:
H;
$C_{1-12}$ alkyl, wherein one or more non-adjacent, non-terminal C atoms may be replaced with O, S, COO or CO; and
an aromatic or heteroaromatic group $Ar^5$ which is unsubstituted or substituted with one or more substituents.

10. A composition comprising a compound of formula (I) according to claim 1 and an electron-donating material capable of donating an electron to the compound.

11. A formulation comprising a compound according to claim 1 dissolved or dispersed in one or more solvents.

12. An organic photodetector comprising: an anode; a cathode; and a photosensitive organic layer disposed between the anode and cathode, wherein the photosensitive organic layer comprises a donor compound and an acceptor compound according to claim 1.

13. A method of forming an organic photodetector according to claim 12 comprising formation of the photosensitive organic layer over one of the anode and cathode, and formation of the other of the anode and cathode over the photosensitive organic layer.

14. A method according to claim 13 wherein formation of the photosensitive organic layer comprises deposition of a formulation comprising the compound dissolved or dispersed in one or more solvents and evaporation of the one or more solvents.

15. A photosensor comprising a light source and an organic photodetector according to claim 12 configured to detect light emitted from the light source.

16. A photosensor according to claim 15 wherein the light source emits light having a peak wavelength greater than 750 nm.

17. A photosensor according to claim 15 configured to receive a sample in a light path between the organic photodetector and the light source.

18. A method of determining the presence and/or concentration of a target material in a sample, the method comprising illuminating the sample and measuring a response of an organic photodetector according to claim 12 configured to receive light emitted from the sample upon illumination.

19. A method according to claim 18 wherein the organic photodetector is the organic photodetector of a photosensor.

* * * * *